(12) United States Patent
Ritter

(10) Patent No.: US 7,077,284 B2
(45) Date of Patent: Jul. 18, 2006

(54) BICARBONATE CONTAINER WITH TWO-CHANNEL PLUG-IN CONNECTOR FOR A HEMODIALYSIS APPARATUS

(76) Inventor: Frank Ritter, Pfarrer-Singer-Strasse 1, 67745 Eppishausen (DE)

( * ) Notice: Subject to any disclaimer, the term of this patent is extended or adjusted under 35 U.S.C. 154(b) by 0 days.

(21) Appl. No.: 11/198,978

(22) Filed: Aug. 8, 2005

(65) Prior Publication Data

US 2006/0043012 A1    Mar. 2, 2006

(30) Foreign Application Priority Data

Aug. 18, 2004 (DE) ............... 10 2004 039 989

(51) Int. Cl.
*A61J 1/00* (2006.01)
*B65D 1/00* (2006.01)
*B65B 1/04* (2006.01)
*A61M 39/00* (2006.01)
*A61M 1/14* (2006.01)

(52) U.S. Cl. ............... 220/501; 220/521; 141/311 R; 141/383

(58) Field of Classification Search ............ 210/232, 210/453, 469, 541; 220/501, 521; 206/438; 141/18, 22, 67, 285, 311 R, 326, 346, 383; 604/403, 406; 285/123.1, 124.1

See application file for complete search history.

(56) References Cited

U.S. PATENT DOCUMENTS 5,540,265 A * 7/1996 Polaschegg et al. ........ 141/301
5,543,118 A * 8/1996 Kaufman .................... 422/292

FOREIGN PATENT DOCUMENTS

EP         0 575 970 A2 *   6/1993

* cited by examiner

*Primary Examiner*—John S. Kim
(74) *Attorney, Agent, or Firm*—Klaus J. Bach

(57) ABSTRACT

In a bicarbonate container for one-time use with a hemodialysis apparatus which container consists of a bottom part with a trough for containing the bicarbonate, a cover for closing the trough and a two-channel plug-in connector for connection to a dialysis apparatus, the bottom part and the top part include flanges which are joined and form therebetween a conduit channel extending from one end of the container where the plug-in connector is disposed to the other end of the container for conducting liquid supplied through one of the plug-in connector channels through the bicarbonate filling of the trough of the container in which the bicarbonate is disposed to the other channel of the plug-in connector.

11 Claims, 4 Drawing Sheets

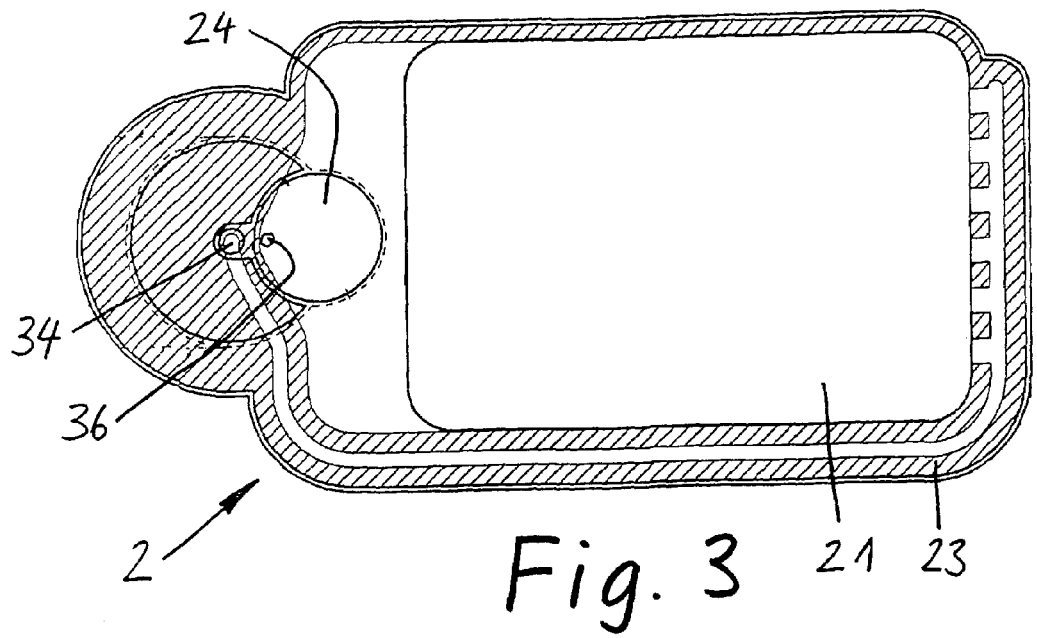
Fig. 3
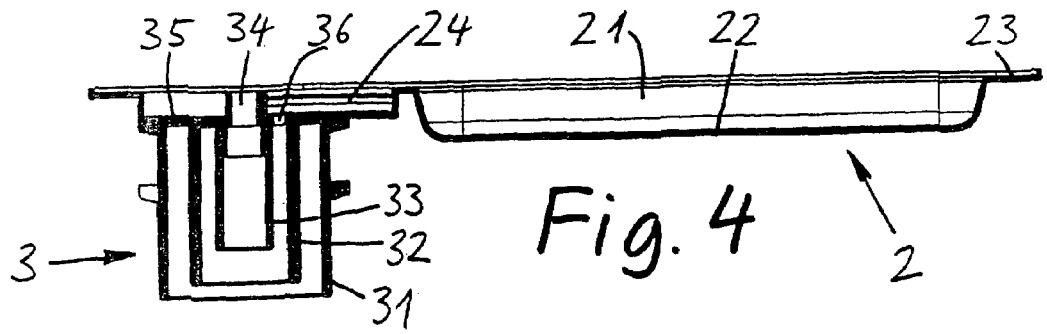
Fig. 4
Fig. 5
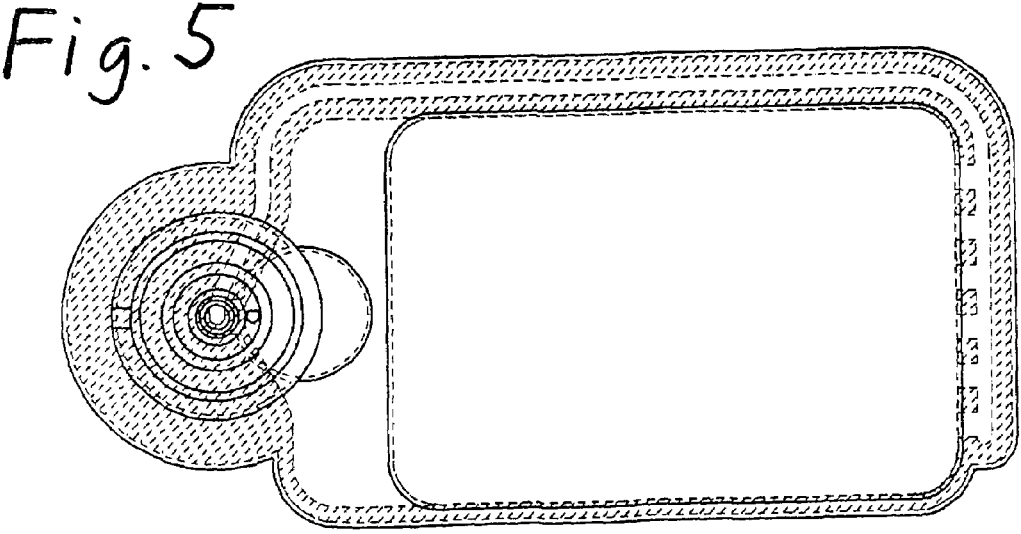

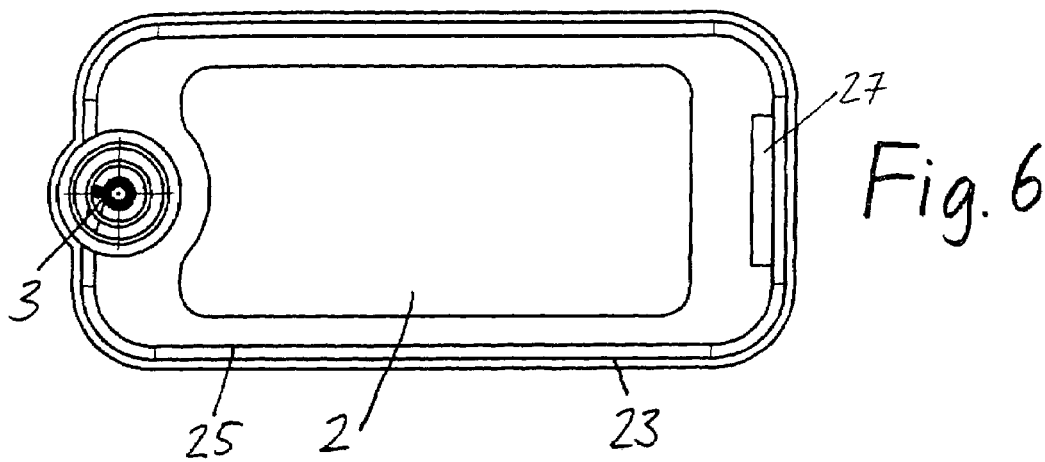
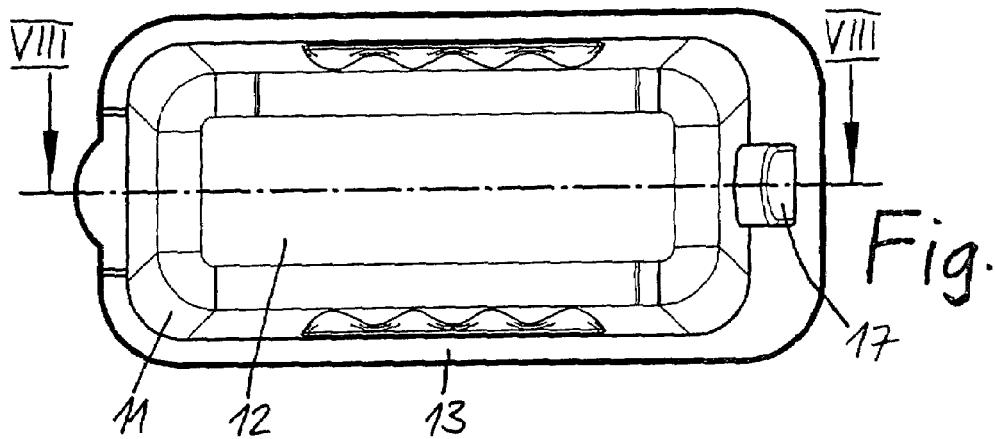
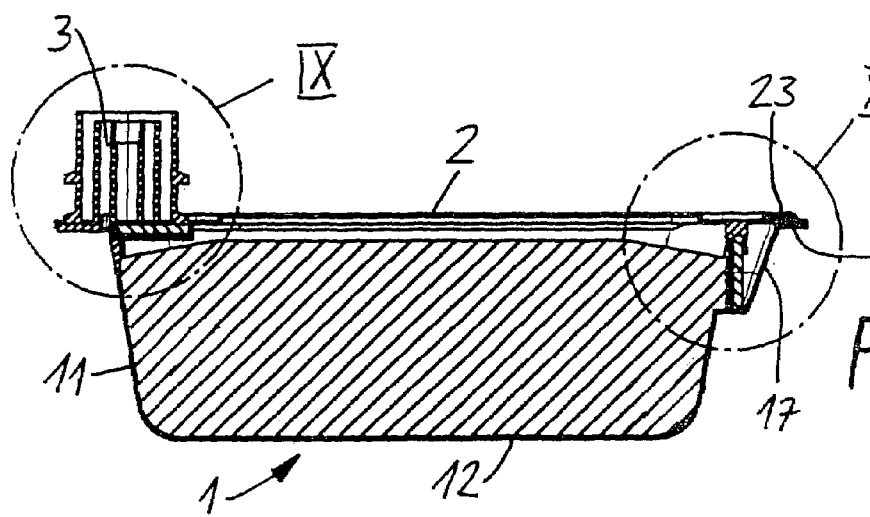

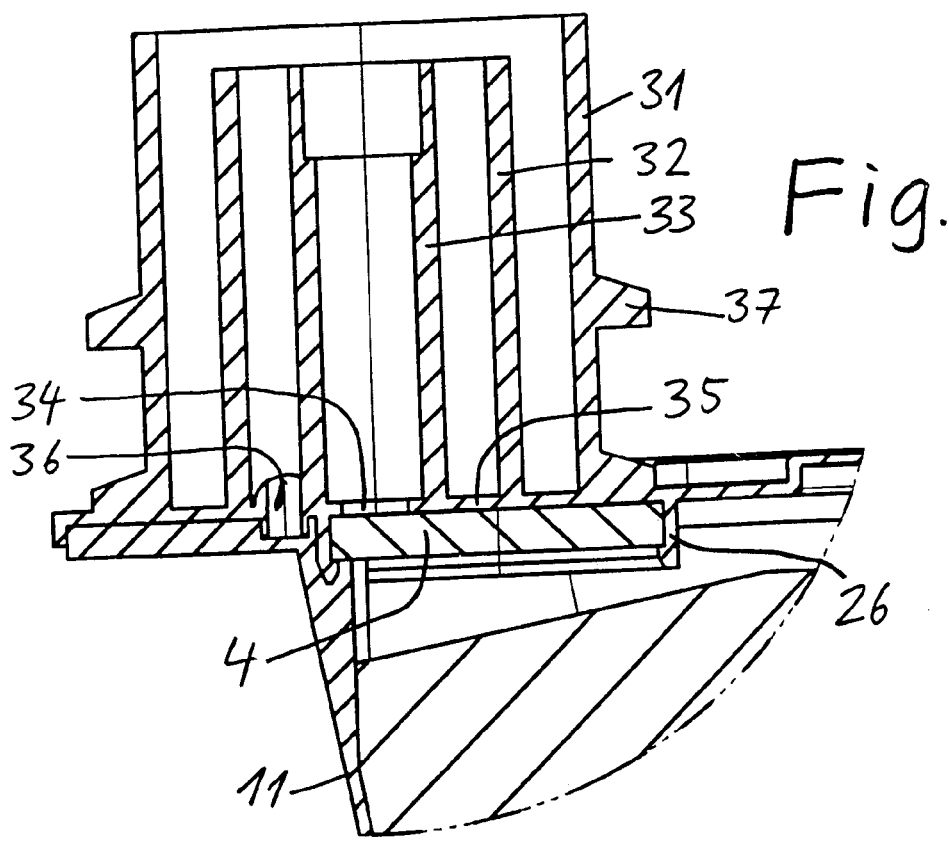
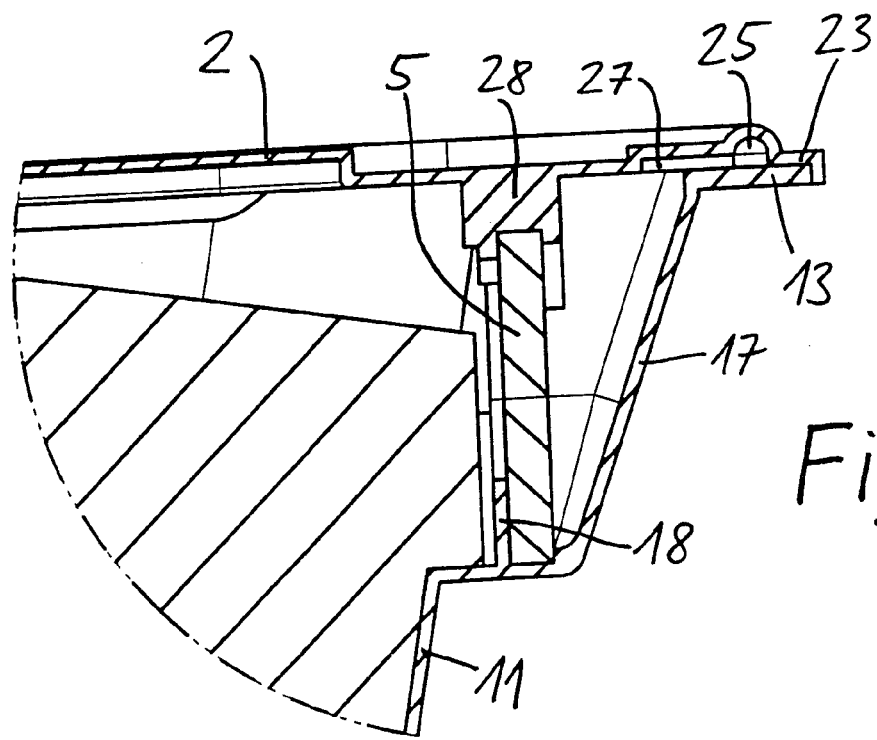

BICARBONATE CONTAINER WITH TWO-CHANNEL PLUG-IN CONNECTOR FOR A HEMODIALYSIS APPARATUS

BACKGROUND OF THE INVENTION

The invention relates to a bicarbonate container for one time use in dialysis apparatus for hemodialysis that is a rigid plastic container including a two-channel plug-in connector for connection of the container to a dialysis apparatus.

A bicarbonate container with a two-channel plug-in connector is already known from EP-0 575 970 A2, wherein the container is shown as a flexible bag. Since, because of the two-channel plug-in connector for the connection to a dialysis apparatus, the inlet and outlet for the solution circuit are disposed at the same location of the container, the container must include a conduit which extends within the container from one of the two plug-in connector channels to the opposite end of the container so that the solution can flow through the whole bicarbonate container. In the container disclosed in EP 0 575 970 A2, a flexible hose extends from one of the two plug-in connector channels through the interior of the bag to the end thereof about opposite the plug-in connector.

However, this arrangement requires relatively high manufacturing expenses and, more importantly, the end of the hose is not fixed so that, after filling the bag with bicarbonate, the end of the hose may not be in the most desirable position within the bag whereby the solution conducted through the bag flows only through part of the bicarbonate contained in the bag.

It is the object of the present invention to provide a bicarbonate container for a hemodialysis apparatus which is easy to manufacture and wherein the opening of the duct extending from the plug-in connection to the opposite end of the container is securely arranged at an optimal location.

SUMMARY OF THE INVENTION

In a bicarbonate container for one-time use with a hemodialysis apparatus which container consists of a bottom part with a trough for containing the bicarbonate, a cover for closing the trough and a two-channel plug-in connector for connection to a dialysis apparatus, the bottom part and the top part include flanges which are joined and form therebetween a conduit channel extending from one end of the container where the plug-in connector is disposed to the other end of the container for conducting liquid supplied through one of the plug-in connector channels through the bicarbonate filling of the trough of the container in which the bicarbonate is disposed to the other channel of the plug-in connector. Two embodiments of the invention will be described below in detail with reference to the accompanying drawings:

BRIEF DESCRIPTION OF THE DRAWINGS

FIG. 3 is a horizontal sectional view of the container taken in a plane extending through the conduit extending from the plug-in connector to the opposite end of the container as seen from the bottom, FIG. 4 is a cross-sectional view of the container cover, FIG. 5 is a top view of the assembled container wherein the weld connections between the bottom part and the top part of the container are shown by hatching, FIG. 6 is a top view of a second embodiment of the bicarbonate container according to the invention, FIG. 7 is a bottom view of the bicarbonate container of FIG. 6, FIG. 8 is a cross-sectional view of the bicarbonate container taken along line VIII—VIII of FIG. 7, FIG. 9 is an enlarged representation of the encircled area IX of FIG. 8, and FIG. 10 is an enlarged representation of the encircled area X of FIG. 8.

DESCRIPTION OF THE PREFERRED EMBODIMENTS

Figure 1:
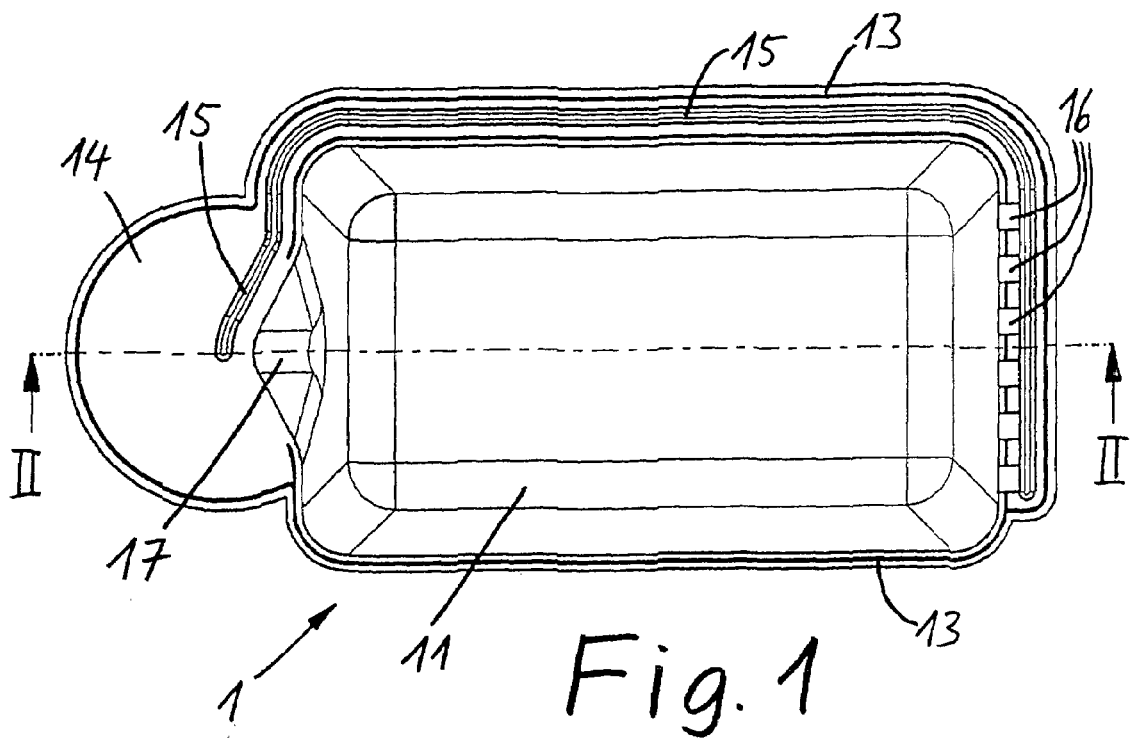
FIG. 1 is a top view of a bottom part of a first embodiment of the bicarbonate container according to the invention.

The bicarbonate container of the first embodiment as shown in FIGS. 1 to 5 comprises a bottom part 1 (FIGS. 1 and 2) and a cover part 2 (FIGS. 3 and 4), which is disposed on the bottom part 1 and welded thereto. Both parts are manufactured from plastic material by injection molding.

The bottom part 1 is in the form of a trough 11 with a bottom 12 and a top flange 13. The trough 11 has, in the embodiment shown, an essentially oblong shape with rounded corners and is slightly narrowing toward the bottom 12. However, the trough 19 could have any other shape, it could for example, be round or semispherical. The flange 13 is flat and extends in the top opening plane of the trough 11 that is around the top opening. The top side of the flange 13 forms a welding surface for welding a corresponding flange surface of the cover part 2 to the bottom part 1.

As shown in FIGS. 3 and 4, the cover part 2 is in the form of a flat tray 21 with a bottom 22 and a flat flange 23 extending around the tray 21. At a narrow side of the tray 21, the flange 23 is enlarged and provided with a plug-in connector 3 which, as shown in the cross-sectional view of FIG. 4, comprises an outer guide sleeve 31. Concentrically, within the outer guide sleeve 31, there are two concentric conductor bushings 32 and 33. The outer guide sleeve 31 forms a guide structure for the mechanical attachment to, and interlocking of, the bicarbonate container with the corresponding complementary plug-in receptacle of the dialysis apparatus. The outer conductor bushing 32 and the inner conductor bushing 33 form two concentric conduit channels providing inlets and, respectively, outlets for the solution conducted through the container. The inner conduit channel formed by the conductor bushing 33 ends in the flange plane in a central opening 34. The outer tubular conduit channel formed between the inner and outer conductor bushings 33, 32 is closed by an end wall 35 provided with a passage 36 extending to a flat circular recesses 24 of the flange 23.

Figure 2:
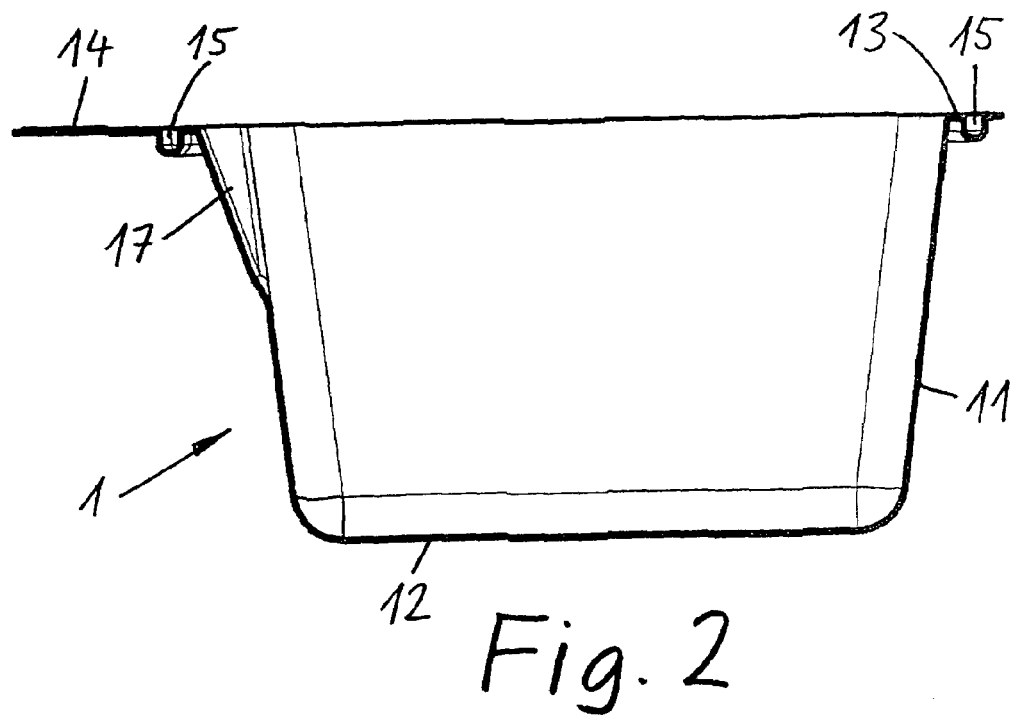
FIG. 2 is a sectional view taken along lines II—II of FIG. 1.

The flange 13 of the bottom part 1 includes in accordance with FIGS. 1 and 2 at one of the narrow sides of the trough 11 a circle segment-shaped extension 14. The extension is complementary in shape to the part of the flange 23 of the cover part 2, which is provided with the plug-in connecter 3. Furthermore, the flange 13 of the bottom part 1 includes a channel 15 extending from the center of the flange extension 14 in the top flange 14 along one of the longitudinal sides of the trough 11 around the trough opening to the narrow side of the trough opposite the flange extension 14 such that the channel 15 is separated from the trough opening by a web-like flange area disposed between the channel 15 and the through opening. This channel also extends essentially over the whole length of the narrow side of the trough 11 opposite the flange extension 14 and is in communication with the trough 11 by a number of inlet passages 16 formed in the flange 13 in spaced relationship.

As further apparent from FIGS. 1 and 2, the trough 11 or rather the bottom part 1 includes at the side below the flange extension 14 an outwardly curved area 17.

FIG. 5 is a top view of the bicarbonate container according to the invention with the cover part 2 disposed on the container bottom part 1 and connected thereto by welding of the flange areas which are in contact with each other.

The area via which the flange 13 of the bottom part 1 is welded together with the flange 23 of the cover part 2 is indicated in FIG. 5 by broken hatching lines. The respective welding surface areas in the cover part 2 are also indicated in FIG. 3 by hatching. It can be seen therefrom that flange areas corresponding to the channel 15 in the flange 13 of the bottom part 1 are not welded together.

From FIG. 5, particularly in connection with FIGS. 1–4, it is apparent that, after the flanges 13 and 23 of the bottom container part 1 and the cover part 2 have been joined, the originally open channel 15 in the bottom part flange 13 is closed by this cover part flange 23 so as to form a conduit which extends from the plug-in connecter 3 through the flange structure to the end of the container opposite the plug-in connector 3. Along the narrow side of the container opposite the plug-in connector 3, the conduit is in communication with the container interior via the inlet passages 16. In the area of the plug-in connector 3, the duct formed by the inner conductor bushing 33. The circular recess 24 of the cover part flange 23 which is in communication, by way of the opening 36 in the bottom wall 35, with the annular flow passage formed between the inner conductor sleeve 33 and the outer conductor sleeve 32 is disposed above the respective end area of the trough 11 which includes the outwardly curved area 17 when the bicarbonate container is assembled.

In this way, the annular conduit of the plug-in connector 3 is in communication with the end of the container interior adjacent the plug-in connector 3 whereas the inner conduit of the plug-in connector 3 is in communication with the opposite end of the container via the conduit formed by channel 15 and the inlet passages 16.

In the bicarbonate container of the second embodiment as shown in FIGS. 6–10 corresponding components are designated by the same reference numerals as used in connection with FIGS. 1–5. The bicarbonate container of the second embodiment also comprises a bottom part 1 and a cover part 2 disposed on the bottom part 1 and welded thereto. Both parts are also manufactured of plastic material by injection molding. The bottom part 1 is again in the form of a trough 11 with a bottom 12 and an upper flange 13 and is of oblong shape with rounded corners and with side walls which extend upwardly from the bottom 12 so as to be slightly inclined outwardly but may have a different shape. The flange 13 is flat and extends in the plane of the opening of the trough 11 around the trough opening. The top side of the flange forms a welding surface for interconnection with a corresponding flange surface of the cover part 2.

The cover part 2 also is provided at its circumference with a flat flange 23 which cooperates with the flange 13 of the bottom part 1. The flange 23 of the cover part 2 includes a channel 25—in contrast to the first embodiment where the channel is formed in the flange of the bottom part—which forms a conduit when the flange 23 of the top part 2 is welded onto the flange 13 of the bottom part 1.

Further, as apparent from FIGS. 6, 8, and 9, the cover part is in the second embodiment—like in the first embodiment—provided with a plug-in connector 3 which, as apparent from the cross-sectional view of FIG. 9—includes an outer guide sleeve 31 and, concentrically within the guide sleeve 31, two co-axial conductor bushings 32 and 33. The inner conduit formed by the inner conductor busing 32 of the plug-in-connector 3 ends again in the plane of the flange 23 which has a central opening 34 which provides for communication with the interior of the container that is the trough 11 of the container bottom part 1. But in this case, the central opening 34 is separated from the trough 1 by a filter disc 4 which is supported at the bottom side of the cover part 2 by a support ring 26.

The tubular conduit formed between the inner and the outer conductor bushings 33, 32 of the plug-in connector is again closed by a bottom wall 35 which has an opening 36, which, in the second embodiment, is in direct communication with the channel 25 formed into the flange 23.

Like in the first embodiment, the trough 11 of the bottom part 1 is provided also in the second embodiment with an outwardly projecting area 17, which in this case however is arranged at the end wall of the trough 11 opposite the plug-in connector 3. The channel 25 formed in the flange 23 of the cover part 2 is in communication with the area 17 formed by the outward projection by way of a flow transfer passage 27. As shown in FIG. 10 in an enlarged sectional view, the interior space of the projection 17 is separated from the interior space of the trough 11 by a filter disc 5 which extends between the trough 11 and the cover part 2 where it is retained by profile members 18 and, respectively, 28.

With the arrangement of the two filter discs 4 and 5 at the opposite ends of the bicarbonate container of the second embodiment, the container can be oriented relative to the dialysis apparatus in any way without the possibility that bicarbonate can be washed out of the trough 11 without being dissolved (In FIG. 8, the carbonate filling is shown by hatching).

For the assembly of the bicarbonate container according to the invention (in both embodiments shown), the bottom part 1 and the cover part 2 which are both manufactured by injection molding only need to be joined along their flanges by welding for example by ultrasound welding (after the bicarbonate has been filled into the trough 11 and the filter discs have been inserted). No hose has to be installed into the container which must be manufactured separately and properly installed so that it cannot be displaced in the bicarbonate filling.

In the embodiments shown, the plug-in connector 3 is formed onto the cover part 2 so that it projects upwardly from the cover part 2 when the bicarbonate container is assembled. This arrangement is advantageous also with regard to a simple design of the injection molding tools since, except for a locking structure 37 at the plug-in connector 3, there are no recesses which would require a slide member in the tool.

However, it is to be understood that other plug-in connector arrangements could be provided on the cover part 2 as well as on the bottom part 1—depending, to a large extent, on the plug-in connector receptacle of the dialysis apparatus—for example a receptacle with non-concentric conductors.

In embodiments wherein the plug-in connector 3 is not disposed on the cover part, but on the bottom part 1 and wherein also the channel 15 is formed in the flange 14 of the bottom part, it would be possible to form only the bottom part 1 by injection molding. The cover 2 could then be simply formed by a foil which, after introduction of the bicarbonate into the trough 11 of the bottom part 1, is placed onto the flange around the trough opening of the bottom part and welded thereto for closing the trough opening and forming in connection with the channel in the flange of the bottom part, the conduit extending between the opposite ends of the trough.

What is claimed is:

1. A bicarbonate container for one-time use with a hemodialysis apparatus in the form of a rigid plastic container with a two-channel plug-in-connector for connection to the hemodialysis apparatus, said container comprising a bottom part (1), a cover part (2) disposed on the bottom part (1), and a two-channel plug-in connector (3) formed with one of the bottom part (1) and the cover part (2), said bottom part (1) including a trough (11) for containing a bicarbonate filling and having a top opening and a flange (13) extending around the top opening and said cover part (2) including a complementary flange (23), said bottom part (1) and said cover part (2) being joined via said flanges (13, 23), said two flanges (13, 23) forming therebetween a conduit channel (15) separated from the interior of the container and extending from one of the two conductor channels of the plug-in connector (3) disposed at one end of the container to the opposite end of the container where the conduit channel (15) is in communication with the trough (11) of the container, the other of the two channels of the plug-in connector (3) being in communication with the trough (11) of the container (1) adjacent said one end of the container.

2. A bicarbonate container according to claim 1, wherein the conduit channel (15, 25) extending from the one of the two channels of the plug-in connector (3) to the opposite end of the container is formed by a channel formed into one of the bottom part and cover part flanges (13, 23), which conduit channel (15, 25) is closed by the joining of the bottom and cover part flanges (13, 23) so as to form a conduit for conducting dialysis liquid from one end of the container to the opposite end of the container.

3. A bicarbonate container according to claim 1, wherein the container is oblong in shape and the plug-in connector (3) is arranged at one of the narrow ends of the oblong container and the conduit channel (15, 25) is in communication with the interior of the container at the other of the narrow ends of the oblong container.

4. A bicarbonate container according to claim 3, wherein, the conduit channel (15, 25) extends at the end of the container opposite the plug-in connector (3) over the width of the container and a number of spaced passages (16) are provided for establishing communication between the conduit channel (15, 25) at the end of the container opposite the plug-in connector (3) and the interior of the container.

5. A bicarbonate container according to claim 1, wherein at the end of the container opposite the plug-in connector (3) the container is provided with an outwardly extending area (17) which is separated from the interior of the container by a filter disc (5).

6. A bicarbonate container according to claim 1, wherein a filter disc (4) is arranged at the end of the container adjacent the plug-in connector (3) between the container interior and the other of the two channels of the plug-in connector (3) which is in communication with the end of the container (1) adjacent the plug-in connector.

7. A bicarbonate container according to claim 1, wherein the bottom part (1) and the cover part (2) are joined along their flanges (13, 23) by ultrasound welding.

8. A bicarbonate container according to claim 1, wherein the plug-in connector (3) is a co-axial plug including an outer guide sleeve (31) and two concentric conductor bushings (32, 33) forming concentric conductor channels.

9. A bicarbonate container according to claim 8, wherein the guide sleeve (31) is provided with a locking element (37) for locking the plug-in connector (3) to a corresponding receptacle of a dialysis apparatus.

10. A bicarbonate container according to claim 1, wherein the bottom part (1) and the cover part (2) on which the plug-in connector (3) is provided, are injection-molded components.

11. A bicarbonate container according to claim 1, wherein the plug-in connector (3) is provided on the bottom part (1) and the cover part (2) consists of a foil which is attached to the flange (13) of the bottom part by one of welding and cementing.

* * * * *